: US005916793A

United States Patent [19]
Filpula et al.

[11] Patent Number: 5,916,793
[45] Date of Patent: Jun. 29, 1999

[54] **ARGININE DEIMINASE DERIVED FROM *MYCOPLASMA ARTHRITIDIS* AND POLYMER CONJUGATES CONTAINING THE SAME**

[75] Inventors: David Ray Filpula, Piscataway; Maoliang Wang, Brunswick, both of N.J.

[73] Assignee: Enzon, Inc., Piscataway, N.J.

[21] Appl. No.: 09/105,908

[22] Filed: Jun. 26, 1998

Related U.S. Application Data

[62] Division of application No. 08/792,283, Jan. 31, 1997, Pat. No. 5,804,183.

[51] Int. Cl.$^6$ .............................. C12N 9/14; C07H 21/04
[52] U.S. Cl. ...................... 435/195; 435/227; 435/252.3; 435/252.33; 435/320.1; 536/23.2; 536/23.1; 536/23.7
[58] Field of Search ..................... 435/195, 227, 435/252.3, 252.33, 320.1; 536/23.2, 23.1, 23.7

[56] References Cited

U.S. PATENT DOCUMENTS

| | | | |
|---|---|---|---|
| 4,179,337 | 12/1979 | Davis et al. | 435/181 |
| 5,122,614 | 6/1992 | Zalipsky | 548/520 |
| 5,349,001 | 9/1994 | Greenwald | 525/408 |
| 5,372,942 | 12/1994 | McGarrity et al. | 435/227 |
| 5,474,928 | 12/1995 | Takaku et al. | 435/228 |

FOREIGN PATENT DOCUMENTS

0414007 A2  2/1991  European Pat. Off. .

OTHER PUBLICATIONS

Ohno, T. et al., "Cloning and Nucleotide Sequence of the Gene Encoding Arginine Deiminase of Mycoplasma arginini," *Infection and Immunity* 58(11):3788–3795 (Nov. 1990).

Harasawa, R. et al., "Nucleotide Sequence of the Arginine Deiminase Gene of *Mycoplasma hominis*," *Microbiol. Immunol.* 36(6):661–665 (1992).

Sugimura, K., et al., "Polymophism in Genes for the Enzyme Arginine Deiminase among Mycoplasma Species," *Infection and Immunity* 61(1):329–331 (Jan. 1993).

Miyazaki, K., "Potent Growth Inhibition of Human Tumor Cells in Culture by Arginine Deiminase Purified from a Culture Medium of a Mycoplasma–Infected Cell Line," *Cancer Res* 50:4522–27 (Aug. 1990).

Takaku, H., et al., "Chemical Modification of Polyethylene Glycol of the Anti–tumor Enzyme Arginine Deiminase from *Mycoplasma arginini*" *Jpn J. Cancer Res.* 84:1195–1200 (Nov. 1993).

Peters, B., et al., *Pegaspargase verses* asparaginase in adult ALL: a pharmacoeconomic assessment *Hospital Formulary* 30(7) (Jul. 1995).

Makrides, S. "Strategies for Achieving High–Level Expression of Genes in *Escherichia coli*," *Microbiological Reviews* 60(3):512–538 (Sep. 1996).

Cregg, J., et al. "Recent Advances in the Expression of Foreign Genes in *Pichia pastoris*," *Bio/Technology* 11:905–910 (Aug. 1993).

Weickmann, J. et al. "Arginine Deiminase from *Mycoplasma arthritidis*," *Journal of Biological Chemistry* 253(17):6016–6020 (Sep. 1978).

Smith, D., et al. "Arginine Deiminase from *Mycoplasma arthritidis*," *Journal of Biological Chemistry* 253(17)6010–6020 (Sep. 1978).

Weickmann, J., et al., "Arginine Deiminase from *Mycoplasma arthritidis*," *Journal of Biological Chemistry* 252(8):2615–2620 (Apr. 1977).

Misawa, S., et al., "High–level expression of *Mycoplasma arginine* demininase in *E. coli* an dits Efficient Renaturation as an Anti–tumor Enzyme," *Journal of Biotechnology* 36:145–155 (1994).

Sarkar, S., et al., "Arginine Auxotrophy in Melanomas Results from a Defect in Arginosuccinate Synthetase Expression," *1996 Annual Retreat on Cancer Research in New Jersey*, Abstract B–5 (May 1996).

Viswanathan, M., et al., "Expression and Purification of Recombinant *E. coli* Asparaginase II . . . " *1996 Annual Retreat on Cancer Research in New Jersey*, Abstract 5 (May 1996).

Lee, S. et al., "Comparison of Arginine Deiminase Isolated from *Pseudomonas putida* and *Mycoplasma arginini* . . . " *1996 Annual Retreat on Cancer Research in New Jersey*, Abstract 6 (May 1996).

Arunakumari, A., et al., "Polyethylene Glycol Conjugated Arginine Deiminase: A Novel Anti–Cancer Therapy" *1996 Annual Retreat on Cancer Research in New Jersey*, Abstract 7 (May 1996).

Takaku, H., et al., "In vivo Anti–Tumor Activity of Arginine Deiminase Purified from *Mycoplasma Arginini*," *Int J. Cancer* 51:244–249 (1992).

Kondo et al., "Cloning and Sequence Analysis of the Arginine Deiminase gene from *Myucoplasma arginini*" *Mol. Gen Genet.* 221:81–86 (1990).

Primary Examiner—Robert A. Wax
Assistant Examiner—Nashaat T. Nashed
Attorney, Agent, or Firm—Roberts & Mercanti LLP

[57] ABSTRACT

A purified arginine deiminase (ADI) obtained from *Mycoplasma arthritidis* having the amino acid sequence of SEQ ID NO:2 as well as an isolated nucleic acid molecule containing a nucleotide sequence encoding the amino acid sequence set forth in SEQ ID NO:1 are disclosed. Other aspects of the invention include an expression vector, a cloned gene for expressing the *Mycoplasma arthritidis* derived ADI, (recombinant) host cells useful in expressing the ADI of the present invention and substantially non-antigenic polymer conjugates containing the ADI of the present invention as well as methods of treating arginine deiminase susceptible conditions in mammals. The arginine deiminase-polymer conjugates have high levels of retained enzyme activity and relatively long circulating lives.

34 Claims, 3 Drawing Sheets

FIG-1  ADI SEQ ID:1

```
ATG TCT GTA TTT GAC AGT AAA TTT AAG GGA ATT CAT GTC TAT TCA    45
GAA ATT GGT GAA CTA GAA ACC GTT TTA GTT CAC GAA CCT GGT AAA    90
GAA ATT GAT TAC ATT ACC CCA GCT CGT TTG GAT GAA TTA TTA TTC   135
TCA GCT ATT CTA GAA AGC CAC GAT GCA AGA AAA GAA CAC AAA GAA   180
TTC GTA GCA GAA CTT AAA AAG CGT GGA ATT AAT GTT GTT GAA TTA   225
GTA GAT CTA ATC GTA GAA ACC TAT GAT TTA GCA TCA AAA GAA GCT   270
AAA GAA AAA CTT TTA GAA GAA TTC CTA GAT GAT TCA GTA CCA GTT   315
CTA TCA GAC GAA CAC CGT GCT ACT GTT AAG AAA TTC TTA CAA AGT   360
CAA AAA TCA ACA AGA TCA TTA GTT GAA TAC ATG ATC GCA GGG ATC   405
ACT AAA CAC GAT TTA AAA ATC GAA TCA GAT TTA GAA TTA ATC GTT   450
GAC CCA ATG CCT AAC TTG TAC TTC ACT CGT GAC CCA TTT GCA TCA   495
GTA GGT AAT GGA GTT ACC ATC CAC TAC ATG CGT TAC AAA GTA AGA   540
CAA CGT GAA ACA TTA TTT AGC CGA TTT GTA TTT TCA AAT CAC CCT   585
AAA CTA GTT AAT ACC CCA TGG TAC TAC GAC CCT GCT GAA GGA TTA   630
ACA ATC GAA GGT GGA GAC GTA TTT ATC TAC AAT AAC GAT ACT TTA   675
GTA GTT GGT GTT TCA GAA AGA ACT GAC TTA CAA ACT ATT ACT TTA   720
TTA GCT AAG AAC ATT AAA GCA AAT AAA GAA TGT GAA TTC AAA CGT   765
ATT GTA GCA ATT AAT GTT CCT AAA TGG ACA AAC CTA ATG CAC TTA   810
GAC ACA TGG TTA ACA ATG CTA GAC AAA GAT AAA TTC TTA TAC TCA   855
CCT ATT GCA AAT GAT GTG TTT AAA TTC TGG GAC TAC GAT TTA GTT   900
AAT GGC GGA GAC GCT CCT CAA CCA GTT GAC AAT GGA TTA CCT CTA   945
GAA GAC TTA TTG AAA TCA ATC ATT GGT AAG AAA CCT ACT CTA ATT   990
CCT ATT GCT GGT GCT GGT GCT TCA CAA ATC GAT ATT GAA CGT GAA  1035
ACC CAC TTT GAC GGA ACA AAC TAC CTA GCT GTA GCT CCT GGA ATT  1080
GTT ATT GGT TAT GCA CGT AAC GAA AAA ACA AAT GCC GCT TTA GAA  1125
GCT GCA GGA ATT ACT GTT CTA CCA TTC AGA GGA AAC CAA CTT TCA  1170
CTT GGA ATG GGA AAT GCT CGT TGC ATG TCA ATG CCT CTA TCA CGT  1215
AAA GAT GTT AAG TGG                                           1230
```

FIG-2  SEQ ID NO:2

```
Met Ser Val Phe Asp Ser Lys Phe Lys Gly Ile His Val Tyr Ser    15
Glu Ile Gly Glu Leu Glu Thr Val Leu Val His Glu Pro Gly Lys    30
Glu Ile Asp Tyr Ile Thr Pro Ala Arg Leu Asp Glu Leu Leu Phe    45
Ser Ala Ile Leu Glu Ser His Asp Ala Arg Lys Glu His Lys Glu    60
Phe Val Ala Glu Leu Lys Lys Arg Gly Ile Asn Val Val Glu Leu    75
Val Asp Leu Ile Val Glu Thr Tyr Asp Leu Ala Ser Lys Glu Ala    90
Lys Glu Lys Leu Leu Glu Glu Phe Leu Asp Asp Ser Val Pro Val   105
Leu Ser Asp Glu His Arg Ala Thr Val Lys Lys Phe Leu Gln Ser   120
Gln Lys Ser Thr Arg Ser Leu Val Glu Tyr Met Ile Ala Gly Ile   135
Thr Lys His Asp Leu Lys Ile Glu Ser Asp Leu Glu Leu Ile Val   150
Asp Pro Met Pro Asn Leu Tyr Phe Thr Arg Asp Pro Phe Ala Ser   165
Val Gly Asn Gly Val Thr Ile His Tyr Met Arg Tyr Lys Val Arg   180
Gln Arg Glu Thr Leu Phe Ser Arg Phe Val Phe Ser Asn His Pro   195
Lys Leu Val Asn Thr Pro Trp Tyr Tyr Asp Pro Ala Glu Gly Leu   210
Thr Ile Glu Gly Gly Asp Val Phe Ile Tyr Asn Asn Asp Thr Leu   225
Val Val Gly Val Ser Glu Arg Thr Asp Leu Gln Thr Ile Thr Leu   240
Leu Ala Lys Asn Ile Lys Ala Asn Lys Glu Cys Glu Phe Lys Arg   255
Ile Val Ala Ile Asn Val Pro Lys Trp Thr Asn Leu Met His Leu   270
Asp Thr Trp Leu Thr Met Leu Asp Lys Asp Lys Phe Leu Tyr Ser   285
Pro Ile Ala Asn Asp Val Phe Lys Phe Trp Asp Tyr Asp Leu Val   300
Asn Gly Gly Asp Ala Pro Gln Pro Val Asp Asn Gly Leu Pro Leu   315
Glu Asp Leu Leu Lys Ser Ile Ile Gly Lys Lys Pro Thr Leu Ile   330
Pro Ile Ala Gly Ala Gly Ala Ser Gln Ile Asp Ile Glu Arg Glu   345
Thr His Phe Asp Gly Thr Asn Tyr Leu Ala Val Ala Pro Gly Ile   360
Val Ile Gly Tyr Ala Arg Asn Glu Lys Thr Asn Ala Ala Leu Glu   375
Ala Ala Gly Ile Thr Val Leu Pro Phe Arg Gly Asn Gln Leu Ser   390
Leu Gly Met Gly Asn Ala Arg Cys Met Ser Met Pro Leu Ser Arg   405
Lys Asp Val Lys Trp                                            410
```

FIG-3

```
a  MSVFDSKFKGIHVYSEIGELETVLVHEPGKEIDYITPARLDELLFSAILE    50
b  ------------------S-------R-----------------------
c  --------N------------------R-----------------------
d  ----SD--N---------D--S------L---------------------- a  SHDARKEHKEFVAELKKRGINVVELVDLIVETYDLASKEAKEKLLEEFLD   100
b  ---------Q------AND------I--VA-------Q---D--I----E
c  ---------QS--KIM-D--------T--VA--------A---EFI-T--E
d  -T----------EI---Q---------V----N-VD-KTQ----KD--- a  DSVPVLSDEHRATVKKFLQSQKSTRSLVEYMIAGITKHDLKIESDLELIV   150
b  --E-----E--KVV-RN--KAK-TS-K---I-M-----Y--G--A-H----
c  ET-----TEANKKA-RA--L-.-P-HEM--F-MS----YE-GV--EN----
d  --E-----P---KA-E-L-K-L---KE-IQ--M-----Y--G-KA-K---- a  DPMPNLYFTRDPFASVGNGVTIHYMRYKVRQRETLFSRFVFSNHPKLVNT   200
b  ----------------------------------------------I--
c  ----------------------F---I--R-----A----R------K-
d  ----------------------------N------K-I-T------K- a  PWYYDPAEGLTIEGGDVFIYNNDTLVVGVSERTDLQTITLLAKNIKANKE   250
b  ------SLK-S---------------------V-------V----
c  ------MKMP----------E-----------D--------------
d  ------MK-S----------------------E-------------- a  CEFKRIVAINVPKWTNLMHLDTWLTMLDKDKFLYSPIANDVFKFWDYDLV   300
b  --------------------------------------------------
c  V------------------------------N------------------
d  -------------------------------------------------- a  NGGDAPQPVDNGLPLEDLLKSIIGKKPTLIPIAGAGASQIDIERETHFDG   350
b  ---AE----E------G--Q---N---V------E----ME--------
c  ---AE---QL-----DK--A---N-E-V----G----TEME-A---N---
d  ---SN-E--V-----DK--E---N---V-----K--TE-ETAV------ a  TNYLAVAPGIVIGYARNEKTNAALEAAGITVLPFRGNQLSLGMGNARCMS   400
b  -----IR--V----S--------------K----H--------------
c  -----IK--L----D---------K--------H--------------
d  -----IK--V-V--S--V--------N--K----K-------------- a  MPLSRKDVKW                                          410
b  ----------
c  ----------
d  ----------
```

ARGININE DEIMINASE DERIVED FROM *MYCOPLASMA ARTHRITIDIS* AND POLYMER CONJUGATES CONTAINING THE SAME

The present application is a divisional of U.S. Ser. No. 08/792,283, filed on Jan. 31, 1997, now U.S. Pat. No. 5,804,183, the contents of which is incorporated by reference herein in its entirety.

BACKGROUND OF THE INVENTION

The present invention is directed to a novel arginine deiminase and long-acting arginine deiminase-containing compositions. In particular the invention is directed to substantially non-antigenic polymer conjugates containing arginine deiminase derived from *Mycoplasma arthritidis* which demonstrate high levels of retained enzyme activity.

Conjugating biologically-active proteins or enzymes to polymers has been suggested to improve one or more of the properties of circulating life, water solubility or antigenicity in vivo. For example, some of the initial concepts of coupling peptides or polypeptides to polyethylene glycol (PEG) and similar water-soluble polymers are disclosed in U.S. Pat. No. 4,179,337, the disclosure of which is incorporated herein by reference. Conjugates are formed by reacting a biologically active material with a several fold molar excess of a polymer which has been modified to contain a terminal linking group. Insulin and hemoglobin were among the first therapeutic agents conjugated. These relatively large polypeptides contain several free ε-amino attachment sites. Several polymers could be attached without significant loss of biologic activity. The conjugation process, however, is not without complications. Excessive polymer conjugation or reactions using molar excesses of polymers beyond certain ratios can result in the formation of inactive conjugates or conjugates having insufficient activity. Problems often result when the active site (i.e. where groups associated with bioactivity are found) on the protein or enzyme becomes blocked as a result of the covalent polymer attachment. This problem can be difficult to avoid because the polymer and protein or enzyme are typically joined in solution-based reactions. Pre-blocking the active sites with reversible materials such as pyridoxal phosphate has been suggested, but the results have been inconsistent. The problems are particularly acute with relatively lower molecular weight proteins and peptides. These bioactive materials often have few attachment sites not associated with bioactivity.

Arginine deiminase (ADI) is one type of enzyme which could benefit from improved polymer conjugation techniques. ADI is an enzyme that hydrolyzes arginine and the depletion of arginine has been postulated to have a killing effect on certain tumors. In particular, the enzyme hydrolyzes the guanidino group of L-arginine into L-citrulline and ammonia. The ADI enzyme is also known as arginine dihydrolase, arginine desiminase or guanidinodesiminase. Although ADI has been obtained from other types of mycoplasma strains as well as other microorganism sources such as pseudomonas and streptococcus, there is variability in the enzyme obtained. In particular, each host strain produces an enzyme having a different number of lysines as well as variations in the active site to produce an enzyme having a different primary sequence, and number and location of lysines.

Several polymer-arginine deiminase conjugates have previously been suggested. See, for example, Jpn. J. Cancer Res. 84, 1195–1200, November 1993 which describes inter alia arginine deiminase from *Mycoplasma arginini* conjugated with methoxy-polyethylene glycol-4,6-dichloro-1,3,5-triazine. The previous arginine deiminase-polymer conjugates prepared to date, however, have been deemed to be unacceptable. One of the chief drawbacks has been that the level of retained arginine deiminase activity provided by highly modified conjugates has been too low in growth inhibition studies. It has been postulated that certain lysine attachment points on the enzyme are intimately connected with the enzyme active site. Therefore, the highly modified conjugates which demonstrate high levels of retained activity were not possible at reasonable expenditures of time and resources.

The present invention addresses these shortcomings.

SUMMARY OF THE INVENTION

It is an object of the invention to provide a novel purified arginine deiminase subunit (hereinafter ADI) obtained from *Mycoplasma arthritidis* having the amino acid sequence of SEQ ID NO:2. In this regard, the invention includes an isolated nucleic acid molecule containing a nucleotide sequence encoding ADI comprising the amino acid sequence set forth in the Figures and SEQ ID NO:1 and SEQ ID NO:2 as well as nucleic acid molecules complementary thereto.

Other aspects of the invention include an expression vector containing a cloned gene for *Mycoplasma arthritidis* derived ADI, (recombinant) host cells useful in expressing the ADI of the present invention and substantially non-antigenic polymer conjugates containing the ADI of the present invention. Still further aspects of the invention include a process for preparing the purified ADI, a process for preparing the aforementioned arginine deiminase-containing substantially non-antigenic polymer-based compositions as well as methods of treating arginine deiminase susceptible conditions in mammals. In this aspect, the treatment methods include administering an effective amount of the compositions described herein, preferably as part of a polymer conjugate, to mammals in need of such therapy.

The substantially non-antigenic polymer is preferably a polyalkylene oxide such as a polyethylene glycol having a molecular weight of from about 600 to about 60,000 and preferably having a molecular weight of about 12,000. Other substantially non-antigenic polymers can also be used. The substantially non-antigenic polymer is preferably covalently conjugated to the ADI via a urethane or similarly hydrolysis resistant linkage in one preferred embodiment. The arginine deiminase-polymer conjugate containing compositions can be included as part of a pharmaceutically-acceptable solution.

The ADI obtained from *M. arthritidis* in accordance with the present invention differs from that previously reported in J. Biol. Chem. Vol. 253 No. 17 pp 6016–6020 (1978) and J. Biol. Chem. Vol. 252 No. 8 pp 2615–2620 (1977). Although both ADI's were obtained from the same American Type Culture Collection ("ATCC") 14152 strain, the ADI described herein has only two cysteines per subunit sequence. The previously reported protein included eighteen cysteines per subunit. Secondly, the ADI of the present invention has a pI of about 5.25 whereas the previously reported ADI obtained from *M. arthritidis* had a pI of 7.0. In addition, the previous work reported above also predicted that the ADI obtained from *M. arthritidis* would have fewer lysines per subunit than the ADI from *M. arginini*. The present inventors, however, have surprisingly discovered that the opposite was the case. A still further point of difference is the fact that the N-terminal residue of the ADI of the present invention is serine (following post-translational removal of methionine), while the previously reported *M. arthritidis* ADI reported alanine as the N-terminal residue. These differences are dramatic and suggest that there is heterogeneity in the ADI obtained from obtained from *M. arthritidis*. A still further possibility is that there is more than one gene for ADI activity associated with *M. arthritidis*.

The arginine deiminase-polymer conjugates of the present invention also afford advantages over those of the prior art. For example, the ADI of the present invention includes several more modifiable lysine positions than prior art ADI, without resorting to the preparation of mutant lysine variants. This allows for substantially more polymer strands to be covalently attached to alternate surface locations without losing tumor cell growth inhibition activity. In addition, the thus formed conjugates have a substantially longer in vivo circulating life than conjugates having similar levels of retained activity prepared according to the prior art.

The term "arginine deiminase susceptible condition" shall be understood to include all disease states, such as tumor growths, cancers, or related conditions, which benefit therapeutically from exogenous arginine deiminase administration. Details concerning such conditions are provided below in Section 4.

For a better understanding of the present invention, reference is made to the following description and its scope will be pointed out in the appended claims.

BRIEF DESCRIPTION OF THE DRAWINGS

FIG. 1 illustrates the complete DNA sequence encoding ADI cloned from *M. arthritidis* ATCC 14152 (1230 bases). The underlined G in the 5-tryptophan codons were changed from A to G by site directed mutagenesis.

FIG. 2 illustrates the translation product (410 amino acids) of the arginine deiminases subunit from *M. arthritidis* ATCC 14152.

FIG. 3 illustrates the amino acid sequence alignment of various arginine deiminases; line a: *M. arthritidis* ATCC 14152 (SEQ ID NO:2); line b: *M. arginini* LBIF (SEQ ID NO:7), see Ohno et al. Infection and Immunity 58: November 1990, pp 3788–3795; line c: *M. hominis* PG21 (SEQ ID NO:8); line d: *M. orale* FERM BP-1970 (SEQ ID NO:9). *M. hominis* and *M. orale* obtained according to R. Harasawa et al. Microbiol. Immunol. 36, pp 661–665, 1992.

DETAILED DESCRIPTION OF THE INVENTION
1. ARGININE DEIMINASE

Accordingly, the present invention includes a novel protein comprising SEQ ID NO:2 having arginine deiminase enzyme activity and a nucleic acid molecule encoding the same. Preferably, the ADI is expressed by a novel gene, comprising the nucleic acid sequence of SEQ ID NO:1, that is isolated from *M. arthritidis*. The present invention also includes methods of making and using the same. In order for the reader to better appreciate the description to follow, the following terms are explained.

The nucleotide sequence of SEQ ID NO:1 is presented in the form of a deoxyribonucleic acid or DNA sequence. However, the artisan will understand that the nucleotide sequence of SEQ ID NO:1 can also be prepared in the form of an RNA molecule, as necessary. Further, the nucleotides comprising the DNA or RNA molecule can also be in the form of nucleotide derivatives or analogs, such as, for example, those listed at 37 C.F.R. § 1.822(p)(1), the disclosure of which is incorporated by reference herein in its entirety. In addition, the invention also encompasses the complement of the nucleotide sequences according to the invention. The artisan will appreciate the fact that the scope of the invention also includes alternate codons which can code for the same amino acid due to the degenerate nature of the genetic code.

"Transfection" refers to the taking up of an expression vector by a host cell, whether or not any coding sequences are in fact expressed. Numerous methods of transfection are known to the ordinarily skilled artisan. For example, transfection is accomplished in the presence of an expression vector and high concentrations of $CaPO_4$, by electroporation, by use of a phage or viral expression vector for insertion into a host cell, by mechanical insertion of nucleic acid, and even by culturing the host cells in the presence of unpackaged nucleic acid fragments. Successful transfection is generally recognized when any indication of the operation of the vector of interest occurs within the host cell.

"Transformation" describes the introduction of a nucleic acid into an organism so that the nucleic acid is replicable, either as an extrachromosomal element or by integration in the host chromosome. Depending on the host cell used, transformation is accomplished using art known methods appropriate to particular host cells. The calcium treatment employing calcium chloride, as described by Cohen, S. N. Proc. Natl. Acad. Sci. (USA), 69: 2110 (1972) and Mandel et al., J. Mol. Biol. 53:154 (1970), is generally used for prokaryotes or other cells that are encapsulated within cellular walls (e.g., many bacterial and/or plant cells). For mammalian cells without such cell walls, the calcium phosphate precipitation method of Graham, F. and van der Eb, A., Virology, 52: 456–457 (1978) is preferred. General aspects of mammalian cell host system transformations have been described in U.S. Pat. No. 4,399,216 issued Aug. 16, 1983. Transformations into yeast are typically carried out according to the method of Van Solingen, P., et al., J. Bact., 130: 946 (1977) and Hsiao, C. L., et al., Proc. Natl. Acad. Sci. (USA) 76: 3829 (1979). However, any other art-known methods for introducing nucleic acid, e.g., DNA, into cells, such as, for example, by nuclear injection or by protoplast fusion, may also be used.

As used herein, the term "complementary" with respect to a nucleic acid refers to the (using Watson-Crick base pairing) opposite strand produced when a first nucleic acid molecule is replicated using that molecule as a template, to form a new, second nucleic acid strand that is complementary to the first. In one aspect of the invention, two nucleic acid molecules are considered to be complementary, each to the other, when they hybridize or bind together under stringent conditions.

The expression "hybridize under stringent conditions" to describe the hybridization of nucleic acid molecules encompassed within the scope of this invention refers to hybridizing under conditions of high hybridization specificity, e.g., low ionic strength and high temperature for washing. Such stringent conditions include, for example, hybridization with 0.15M NaCl/0.015M sodium citrate/0.1% $NaDodSO_4$ at 50° C., or alternatively, in the presence of denaturing agents such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate, at 42° C. for hybridization. "Hybridize under low stringency" refers to hybridizing under conditions of reduced hybridization specificity. Such conditions include, simply by way of example, hybridizing at 42° C. in 20% formamide, 5×SSC, 50 mM sodium phosphate pH 6.8, 0.1% sodium pyrophosphate, 5×Denhardt's solution, and 50 μg/ml salmon sperm DNA, and washing with 2×SSC, 0.1% SDS at 42° C.

Additionally, specific mutations can be introduced into the arginine deiminase gene of the present invention using "site-directed mutagenesis". This is a technique standard in the art, and is conducted, e.g., using a synthetic oligonucleotide primer complementary to a single-stranded phage DNA to be mutagenized except for limited mismatching, representing the desired mutation. Such mutations may include, for example, the deletion, insertion, or substitution of the codons expressing naturally occurring amino acids. Such mutations may confer altered protein characteristics, which may, for example, improve and/or alter the oxidative, thermal, and/or pH stability of the protein. Briefly, in this method, the synthetic oligonucleotide is used as a primer to direct synthesis of a strand complementary to the phage, and the resulting double-stranded DNA is transformed into a phage-supporting host bacterium. Cultures of the transformed bacteria are plated on agar, permitting plaque formation from single cells that harbor the phage. Usually from about 50 up to about 90% of the new plaques will contain the phage having, as a single strand, the mutated form. The plaques are hybridized with kinased synthetic primer at a temperature that permits hybridization of an exact match, but at which the mismatches with the original strand are sufficient to prevent hybridization. Plaques that hybridize with the probe are then selected and cultured, and the DNA is recovered. Thus, the artisan will appreciate that the nucleotide sequence of SEQ ID NO:1 can be conveniently subjected to mutagenesis by art known techniques, e.g., by nucleotide substitution, to produce useful variant alleles. Simply by way of example, the nucleotide sequence of SEQ ID NO:1 has been variously prepared with substitutions providing a T at nucleotide 39, a C at nucleotide 104, an A at nucleotide 206, a G at nucleotide 337, an A at nucleotide 729, a C at nucleotide 830, a C at nucleotide 1023, an A at nucleotide 6, a T at nucleotide 15, a C at nucleotide 18 and/or combinations thereof. In particular, the specific substitution at 337 would change the threonine to alanine.

"Operably linked" refers to a juxtaposition of components, e.g., a regulatory region and an open reading frame, such that the normal function of the components can be performed. Thus, an open reading frame that is "operably linked" to control sequences refers to a configuration wherein the coding sequence can be expressed under the control of these sequences and wherein the DNA sequences being linked are contiguous and, in the case of a secretory leader, contiguous and in reading phase. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Linking is accomplished by ligation at convenient restriction sites. If such sites do not exist, then, for example, synthetic oligonucleotide adaptors or linkers are used in accord with conventional practice.

"Control Sequences" refers to nucleic acid sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize, for example, such control sequences as promoters, polyadenylation signals, and enhancers, to name but a few.

"Expression system" or "expression vector" refers to nucleic acid sequences containing a desired coding sequence and control sequences in operable linkage, so that hosts transformed with these sequences are capable of producing the encoded proteins. To effect transformation, the expression system may be included on a vector; however, the relevant nucleic acid molecule may then also be integrated into the host chromosome.

As used herein, "cell," "cell line," and "cell culture" are used interchangeably and all such designations include progeny. Thus, "transformants" or "transformed cells" includes the primary subject cell and cultures derived therefrom without regard for the number of transfers. It is also understood that all progeny may not be precisely identical in genomic content, due to deliberate or inadvertent mutations. Mutant progeny that have the same functionality as screened for in the originally transformed cell are included. Where distinct designations are intended, it will be clear from the context.

The vectors disclosed herein are suitable for use in host cells over a wide range of prokaryotic and eukaryotic organisms. In general, prokaryotes are preferred for the initial cloning of DNA sequences and construction of the vectors useful in the invention. For example, *E. coli* K12 strain MM 294 (ATCC No. 31,446) is particularly useful. Other microbial strains, simply by way of example, that may be used include *E. coli* strains such as *E. coli* B and *E. coli* X1776 (ATCC No. 31,537). Prokaryotes may also be used for expression. The aforementioned strains, as well as, e.g., *E. coli* strains W3110 (F-, lambda-, prototrophic, ATCC No. 27,325), K5772 (ATCC No. 53,635), and SR101, bacilli such as *Bacillus subtilis*, and other enterobacteriaceae such as *Salmonella typhimurium* or *Serratia marcesans*, and various pseudomonas species, may be used.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., 1977, Gene, 2: 95). pBR322 contains genes for ampicillin and tetracycline resistance and thus provides easy means for identifying transformed cells. Similarly, the pUC plasmids provide convenient cloning vectors with DNA molecules for selection and replication (Yanisch-Perron, et al., 1985, Gene 33:103–119, the disclosure of which is incorporated by reference herein in its entirety). The pBR322 plasmid, or other microbial plasmid or phage, must also contain, or be modified to contain, promoters that can be used by the microbial organism for expression of its own proteins.

"Plasmids" are designated by a lower case "p" preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

Those promoters most commonly used in recombinant DNA construction include the beta-lactamase (penicillinase) and lactose promoter systems (Chang et al., 1978 Nature, 375: 615; Itakura et al., 1977, Science, 198: 1056; Goeddel et al., 1979, Nature, 281: 544) and a tryptophan (trp) promoter system (Goeddel et al., 1980, Nucleic Acids Res., 8: 4057; EPO Appl. Publ. No. 0036,776). While these are the most commonly used, other microbial promoters have been discovered and utilized, and details concerning their nucleotide sequences have been published, enabling a skilled worker to ligate them functionally with art known vectors, e.g., plasmid vectors.

Simply by way of example, transcriptional regulation in *E. coli* may be achieved with any of the following inducible promoters: lac, trp, phoA, araBAD, T7, and derivatives of the lambda $P_L$ and $P_R$ promoters as well as others well known to the art (e.g., Makrides, 1996, Microbiol. Rev. 60:512–538, the disclosure of which is incorporated by reference herein in its entirety). Preferably, the promoter is the $O_L/P_R$ hybrid promoter, described by Scandella et al., in co-owned U.S. Pat. No. 5,162,216, the disclosure of which is incorporated by reference herein in its entirety, is employed.

In addition to prokaryotes, eukaryotic microbes, such as yeast cultures, may also be used. *Saccharomyces cerevisiae*, or common baker's yeast, is the most commonly used among eukaryotic microorganisms, although a number of other strains are commonly available. For expression in Saccharomyces, the plasmid YRp7, for example (Stinchcomb et al., 1979, Nature, 282: 39; Kingsman et al., 1979, Gene, 7: 141; Tschemper et al., 1980, Gene, 10: 157), is commonly used. This plasmid already contains the trp1 gene that provides a selection marker for a mutant strain of yeast lacking the ability to grow in tryptophan, for example, ATCC No. 44,076 or PEP4-1 (Jones, 1977, Genetics, 85: 12). The presence of the trp1 lesion as a characteristic of the yeast host cell genome then provides an effective environment for detecting transformation by growth in the absence of tryptophan.

The *Pichia pastoris* expression system has been shown to achieve high level production of several proteins (Cregg, J. M. et al., 1993, *Bio/Technology* 11: 905–910, the disclosure of which is incorporated by reference herein in its entirety) and may be employed to express ADI as a soluble protein in the cytoplasm of *Pichia pastoris*.

Suitable promoting sequences in yeast vectors include the promoters for 3-phosphoglycerate kinase (Hitzeman et al., J. 1980, Biol. Chem., 255: 2073) or other glycolytic enzymes (Hess et al., 1968, J. Adv. Enzyme Reg., 7: 149; Holland et al., 1978, Biochemistry, 17: 4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the MRNA and transcription termination. Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

An origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Satisfactory amounts of protein are produced by cell cultures; however, refinements, using a secondary coding sequence, serve to enhance production levels even further. One secondary coding sequence comprises dihydrofolate reductase (DHFR) that is affected by an externally controlled parameter, such as methotrexate (MTX), thus permitting control of expression by control of the methotrexate concentration.

Although any suitable strain of *M. arthritidis* can be employed as a source of the novel gene according to the invention, preferably, the *M. arthritidis* strain that is employed is the strain deposited in the American Type Culture Collection ("ATCC") as accession number 14152.

A gene capable of expressing the novel arginine deiminase enzyme according to the invention is preferably isolated from the *M. arthritidis* genome by primer directed nucleic acid amplification and thereafter cloned into any suitable screening vector and expression system (Molecular Cloning: A Laboratory Manual, Second Edition, J. Sambrook, E. F. Fritsch and T Maniatis, Eds., Cold Spring Harbor Press, 1989). The artisan will appreciate that any appropriate art-known nucleic acid amplification method, utilizing suitable primers, can be employed. Preferably, the amplification method is the polymerase chain reaction, as described, simply by way of example, by Mullis, in U.S. Pat. Nos. 4,683,195, 4,683,202 and 4,800,159, the disclosures of which are incorporated herein by reference in their entireties.

The artisan will also appreciate that any plasmid, phage or cosmid expression vector, inserted into the respective host cells, may be employed to express, screen and identify an amplified nucleic acid fragment encoding the arginine deiminase of the invention. Preferably, an *Escherichia coil* expression system is employed. More preferably a GX6712/pGX9401 *Escherichia coli* expression system is employed.

The primers used for amplification of the ADI gene according to the examples provided hereinbelow were oligonucleotides having the sequences of SEQ ID NOs 3 and 4, respectively. These primers successfully amplified the entire gene. As indicated in the Examples below, the primer of SEQ ID NO:3 differed from the corresponding N-terminal encoding region of the isolated gene (SEQ ID NO:1) by three base substitutions which did not alter the encoded peptide sequence. The three base substitutions, the numbering of which is based on the numbering of SEQ ID NO:1, are as follows: at base 6 is A is substituted for T; at base 15 T is substituted for C; and at base 18 C is substituted for T.

Thus, the successful amplification of the entire gene having a sequence comprising SEQ ID NO:1 was surprising, since, as a result of the aforementioned mismatches, relative to the naturally occurring N terminal sequence of the isolated ADI gene, the SEQ ID NO:3 primer annealed poorly to the target fragment, thus providing an explanation for the very weak PCR signal that resulted from amplification using the primer of SEQ ID NO:3.

The artisan will also appreciate that a primer based on the exact naturally occurring N-terminal sequence of SEQ ID NO:1 will also readily serve, with even better efficacy, at amplifying the ADI gene according to the invention.

Clones provided according to the examples hereinbelow include plasmid pEN232 comprising the ADI gene in expression vector pGX 9401. The initial two PCR isolates of the *M. arthritidis* ADI gene were also cloned into plasmid pBluescript II SK(−) (Stratagene Cloning Systems, La Jolla, Calif.) and designated pEN241 and pEN242. The N-terminal fragment cloning of an ADI gene segment into pBluescript II SK(−), described in Example 1B, included two independently analyzed clones designated pEN245 and pEN246. Independent transformations of E. coli DH5-alpha (GIBCO BRL, Gaithersburg, Md.) with plasmids pEN241, pEN242, pEN245 and pEN246 produced E. coli clones designated EN243, EN244, EN247 and EN248, respectively.

Once a transfected or transformed host cell is obtained, a nucleic acid molecule that includes a sequence according to SEQ ID NO:1 is readily produced by culturing the host cell, and extracting and isolating the nucleic acid as desired, by methods well known to the art. Depending on the degree of purity desired, the extracted nucleic acid may be isolated, or where desired, substantially isolated by art known methods, to be free or substantially free of contaminating host cell proteins and nucleic acids. Similarly, host cells expressing the arginine deiminase protein encoded by the expression vectors according to the invention are cultured by methods suitable for the selected host cell.

For example, host cells are cultured until desired cell densities are achieved, and then the cells are separated from the growth medium and the protein is extracted and thereafter renatured according to art-known methods. In particular, the cells are separated from the culture medium to form a cell paste. The cell paste is then re-suspended and then disrupted by standard methods, e.g., mechanical, ultrasonic and/or chemical disruption. Preferably, the cells are disrupted by processing in a Microfluidizer (Microfluidics Corp. Newton Mass.) followed by washing with a suitable surfactant, such as, for example, Triton X-100.

The resulting homogenate is denatured with guanidine HCl, 6M and then diluted into refolding buffer (e.g., 10 mM $K_2PO_4$, pH 7.0), particulates removed, e.g., by centrifugation, followed by purification of the supernatant by standard methods, e.g., by Q Sepharose column chromatography, to provide substantially purified arginine deiminase, e.g., with a purity of about 60% and having a specific activity ranging from about 3 to about 25 IU/mg, or more, and preferably from about 5 to about 20 IU/mg. Additional concentration of the ADI can be achieved using a Centriprep-10, Amicon, Inc. Beverly, Mass.. Other similarly operating columns can also be used if desired.

2. NON-ANTIGENIC POLYMERS

In order to form the polymer-arginine deiminase conjugates of the present invention, polymers such as poly (alkylene oxides) (PAO's) are converted into activated forms, as such term is known to those of ordinary skill in the art. Thus, one or both of the terminal polymer hydroxyl end-groups, (i.e. the alpha and omega terminal hydroxyl groups) are converted into reactive functional groups which allows covalent conjugation. This process is frequently referred to as "activation" and the product is called an "activated poly(alkylene oxide)". Polymers containing both alpha and omega linking groups are referred to as bis-activated polyalkylene oxides. Other substantially non-antigenic polymers are similarly "activated" or functionalized. Among the substantially non-antigenic polymers, mono-activated polyalkylene oxides (PAO's), such as monomethoxy-polyethylene glycols are preferred. In alternative embodiments, homobifunctional bis-activated polymers such as bis-succinimidyl carbonate activated PEG are preferred.

The activated polymers are thus suitable for reacting with arginine deiminase and forming ADI-polymer conjugates wherein attachment preferably occurs at either the amino terminal α-amino group or ε-amino groups of lysines found on the ADI.

In one preferred aspect of the invention, carbamate (urethane) linkages are formed using the ADI ε amino groups and the activated polyalkylene oxides. Preferably, the carbamate linkage is formed as described in commonly owned U.S. Pat. No. 5,122,614, the disclosure of which is hereby incorporated by reference. This patent discloses the formation of mono- and bis- N-succinimidyl carbonate derivatives of polyalkylene oxides (SC-PEG). Alternatives include para-nitrophenyl carbonate and carbonyl imidazole activated polymers.

In another aspect of the invention, polymers activated with amide-forming linkers such as cyclic imide thione-activated polyalkylene oxides, succinimidyl esters or the like are used to effect the linkage between the arginine deiminase and polymer terminal groups, see for example, U.S. Pat. No. 5,349,001 to Greenwald, et al., the disclosure of which is incorporated herein by reference. Still other aspects of the invention include using other activated polymers to form covalent linkages of the polymer with the arginine deiminase via ε amino or other groups. For example, isocyanate or isothiocyanate forms of terminally activated polymers can be used to form urea or thiourea-based linkages with the lysine amino groups. PEG-dialdehyde can also be reacted with the arginine deiminase followed by reduction with $NaCNBH_3$ to form a secondary amine linkage.

Suitable polymers will vary substantially by weight, however polymers having molecular weights ranging from about 200 to about 60,000 are usually selected for the purposes of the present invention. Molecular weights of from about 1,000 to about 40,000 are preferred and 2,000 to about 20,000 are particularly preferred.

The polymeric substances included are also preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

As an alternative to PAO-based polymers, effectively non-antigenic materials such as dextran, polyvinyl pyrrolidones, polyacrylamides, polyvinyl alcohols, carbohydrate-based polymers and the like can be used. Indeed, the activation of alpha and omega terminal groups of these polymeric substances can be effected in fashions similar to that used to convert polyalkylene oxides and thus will be apparent to those of ordinary skill. Those of ordinary skill in the art will realize that the foregoing list is merely illustrative and that all polymer materials having the qualities described herein are contemplated. For purposes of the present invention, "effectively non-antigenic" means all materials understood in the art as being nontoxic and not eliciting an appreciable immunogenic response in mammals.

3. REACTION CONDITIONS

Conjugation reactions, sometimes referred to as pegylation reactions, are generally carried out in solution with from about an equimolar to about a several fold molar excess of activated polymer. Preferably, the molar excess of activated polymer is about 50-fold, or greater. One way to maintain the arginine deiminase bioactivity is to substantially avoid including those arginine deiminase lysines associated with the active site in the polymer coupling process. Given the usually non-specific nature of the coupling reaction, this theoretical step is often difficult to achieve in practice. The process of the present invention, however, provides arginine deiminase conjugates having high levels of retained activity by using arginine deiminase obtained from M. arthritidis, which has a substantial increase in the number of available of lysines for polymer attachment, and avoiding the use of an excessively high molar excess, e.g., more than about 100 fold, of activated polymer during the conjugation reactions.

Thus, the conjugation conditions include reacting arginine deiminase obtained from *M. arthritidis* with a suitably activated substantially non-antigenic polymer such as SC-PEG in a suitable buffer solution in a ratio of activated polymer to arginine deiminase of from about 50 to about 100 fold.

The conjugation reaction is carried out under relatively mild conditions to avoid inactivating the arginine deiminase. Mild conditions include maintaining the pH of the reaction solution in the range of 6–8 and the reaction temperatures within the range of from about 0–30° C. and preferably at about 4° C. for about one hour. Suitable buffers include buffer solutions able to maintain the preferred pH range of 6–8 without interfering with the conjugation reaction. A non-limiting list of suitable buffers includes, e.g., phosphate buffer, citrate buffer, acetate buffer.

Although the reaction conditions described herein may result in some unmodified arginine deiminase, the unmodified arginine deiminase can be readily recovered and recycled into future batches for additional conjugation reactions.

The conjugation reactions of the present invention initially provide a reaction mixture or pool containing arginine deiminase conjugates having from about 16 to about 22 strands of polymer per subunit of enzyme (31 total lysines), unreacted arginine deiminase, if any, and unreacted polymer. After the unreacted species have been removed, compositions containing the arginine deiminase-polymer conjugates are recovered. These compositions have at least about 20% of the biological activity associated with the native or starting arginine deiminase as measured using an assay such as that described below in Example 3. In preferred aspects of the invention, however, the conjugates have at least about 30% of the biological activity associated with starting arginine deiminase and most preferably, the conjugates have at least about 90% of the biological activity associated with starting arginine deiminase.

A representative conjugation reaction is set forth below:

An about 50 fold molar excess of activated polymer is dissolved in Water For Injection (pH approximately 6.0) and then added to an *M. arthritidis* arginine deiminase solution adjusted to about pH 8.0 with a suitable buffer such as a phosphate or borate buffer. The reaction is allowed to incubate at about 4° C., at about pH 8.0, for a suitable time, such as about 1 hour, with continuous gentle mixing. Thereafter, the conjugation reaction is stopped, for example with a several-fold molar excess of arginine or glycine. The unmodified arginine deiminase present in the reaction pool, if any, after the conjugation reaction has been quenched, can be recovered for recycling into future reactions using ion exchange or size exclusion chromatography or similar separation techniques. Preferably, solutions containing the conjugates of the present invention contain less than about 5% unmodified arginine deiminase.

If desired, the arginine deiminase-polymer conjugates are isolated from the reaction mixture to remove high molecular weight species, and unmodified arginine deiminase. The separation process is commenced by placing the mixed species in a buffer solution containing from about 1–10 mg/ml of the arginine deiminase-polymer conjugates. Suitable solutions have a pH of from about 6.0 to about 9.0 and preferably from about 7.5 to about 8.5. The solutions preferably contain one or more buffer salts selected from KCl, NaCl, $K_2HPO_4$, $KH_2PO_4$, Na2HPO$_4$, $NaH_2PO_4$, $NaHCO_3$, $NaBO_4$, and NaOH. Sodium phosphate buffers are preferred.

Depending upon the reaction buffer, the arginine deiminase polymer conjugate solution may first have to undergo buffer exchange/ultrafiltration to remove any unreacted polymer. For example, the PAO-Arginine deiminase conjugate solution can be ultra-filtered across a low molecular weight cut-off (10,000 to 30,000 Dalton) membrane to remove most unwanted materials such as unreacted polymer, surfactants, if present, or the like.

Fractionation of the ADI-polymer conjugates, if desired, can also be carried out using an anion exchange chromatography medium. Such media are capable of selectively binding PAO-arginine deiminase conjugates via differences in charge which vary in a somewhat predictable fashion. For example, the surface charges of ADI is determined by the number of available charged amino acids on the surface of the protein. Of these charged amino acids, lysine residues serve as the point of potential attachment of polyalkylene oxide conjugates. Therefore, arginine deiminase conjugates will have a different charge from the other species to allow selective isolation. The use of strongly polar anion exchange resins such as quaternary amine anion exchange resins are especially preferred for the method of the present invention. Included among the commercially available quaternary anion exchange resins suitable for use with the present invention are Q-HD, QA TRISACRYL® and QMA-SPHEROSIL®, quaternary amine resins coated onto a polymer matrix, manufactured by IBF of Garenne, France, for Sepracor of Marlborough, Mass.; TMAE650M®, a tetramethylamino ethyl resin coated onto a polymer matrix, manufactured by EM-Separators of Gibbstown, N.J.; QAE550C®, and SUPERQC®, each a quaternary amine resin coated onto a polymer matrix and manufactured by TosoHaas of Montgomeryville, Pa. QMA Accell, manufactured by Millipore of Milford, Mass. and PEI resins manufactured by JT Baker of Phillipsburg, N.J., may also be used. Other suitable anion exchange resins e.g. DEAE resins can also be used.

For example, the anion exchange resin is preferably packed in a column and equilibrated by conventional means. A buffer having the same pH and osmolality as the polymer conjugated arginine deiminase solution is used. The elution buffer preferably contains one or more salts selected from KCl, NaCl, $K_2HPO_4$, $KH_2PO_4$, $Na_2HPO_4$, $NaH_2PO_4$, $NaHCO_3$, $NaBO_4$ and $(NH_4)_2CO_3$. The conjugate-containing solution is then adsorbed onto the column with the high molecular weight species and unreacted polymer not being retained. At the completion of the loading, a gradient flow of an elution buffer with increasing salt concentrations is applied to the column to elute the desired fraction of polyalkylene oxide-conjugated arginine deiminase. The eluted pooled fractions are preferably limited to uniform mono- and bis-arginine deiminase polymer conjugates after the anion exchange separation step. Any unconjugated arginine deiminase species can then be back washed from the column by conventional techniques. If desired, the arginine deiminase species can also be separated via additional ion exchange chromatography or size exclusion chromatography. The temperature range for elution is between about 4° C. and about 25° C. Preferably, elution is carried out at a temperature of from about 6° C. to about 22° C. Fraction collection may be achieved through simple time elution profiles.

4. METHODS OF TREATMENT

Another aspect of the present invention provides methods of treatment for various medical conditions in mammals. The methods include administering an effective amount of arginine deiminase-polymer conjugates which have been prepared as described herein to a mammal in need of such treatment. The conjugates are useful for, among other things, treating arginine deiminase-susceptible conditions or conditions which would respond positively or favorably as these terms are known in the medical arts to arginine deiminase-based therapy. Thus, without limitation, the arginine deiminase conjugates can be used to treat conditions, including, carcinomas deficient in the enzyme argininosuccinate synthetase, e.g., melanoma (Sugimura et al., 1992, Melanoma Res. 2:191–196) and nitric oxide related conditions, e.g., conditions that may be treated or ameliorated by modulation of nitric oxide synthase (Nagasaki et al, 1996, J. Biol. Chem. 271:2658–2662; Xia et al., 1996, Proc. Natl. Acad. Sci. USA 93:6770–6774) and certain dietary applications, e.g., modulating the therapeutic effects of low protein diets (Narita et al., 1995, Proc. Natl. Acad. Sci. USA 92:4552–4556).

The amount of the arginine deiminase-polymer conjugate administered to treat the conditions described above is based on the arginine deiminase activity of the polymeric conjugate. It is an amount that is sufficient to significantly effect a positive clinical response. The maximal dose for mammals including humans is the highest dose that does not cause clinically-important side effects. For purposes of the present invention, such clinically important side effects are those which would require cessation of therapy such as, for example, hypersensitivity reactions and/or other immunogenic reactions.

Naturally, the dosages of the arginine deiminase-based compositions will vary somewhat depending upon the arginine deiminase moiety and polymer selected. In general, however, the conjugate is administered in amounts ranging from about 300 to about 3000 IU/m$^2$ of arginine deiminase per day, based on the mammal's condition. The range set forth above is illustrative and those skilled in the art will determine the optimal dosing of the conjugate selected based on clinical experience and the treatment indication.

The ADI-polymer conjugates of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions will be chiefly by the parenteral route although oral or inhalation routes may also be used depending upon the needs of the artisan.

EXAMPLES

The following examples serve to provide further appreciation of the invention but are not meant in any way to restrict the effective scope of the invention.

Example 1
Expression of *M. arthritidis* ADI Gene in *E. Coli*
A. Isolation and Cloning of ADI Gene

*M. arthritidis* strain 14152 was obtained from the American Type Culture Collection. The arginine deiminase gene of *M. arthritidis* was amplified by a polymerase chain reaction (PCR) using the primer pair 5'GGCAATCGATGT CTGTATTTGACAGTA-3'(SEQ ID NO:3) and 5'-TGAGGATCCTTACTACCACTTAACATCTTTACG-3' (SEQ ID NO:4) derived from the published sequence of *M. arginini* LBIF (Ohno, T. et al. 1990) "Cloning and Nucleotide Sequence of the Gene Encoding Arginine Deiminase of *Mycoplasma arginini*" *Infect Immun.*, 58: 3788–3795, the contents of which are incorporated herein by reference.

The PCR amplification was conducted by standard methods (as reviewed by Saiki et al., 1989, *PCR Technology*, pages 7–16; Ed. Henry A. Erlich, Stockton Press) with the following parameters.

The reaction was conducted in a volume of 100 microliters, with a PCR buffer of 10 millimolar Tris-HCl, pH 8.3, 50 millimolar KCl, 2 millimolar MgCl$_2$, and 200 $\mu$M of each deoxynucleotide triphosphate (dATP, dCTP, dGTP and dTTP) and 2.5 units of Taq DNA polymerase (from Perkin Elmer). Thirty cycles of amplification were carried out in a Perkin Elmer PCR system 9600 thermal cycler, set to denature at 94 degrees C. for 60 seconds, anneal at 37° C. for 180 seconds and extend at 72 degrees C. for 120 seconds.

After PCR amplification, two rather faint bands representing amplified fragments were observed on agarose gel analysis at 1.4 kb and 1.2 kb. Samples of each fragment, respectively, were excised from the gel, purified and cloned as a ClaI-BamHI fragment directly into expression plasmid pGX9401 in the manner disclosed by Filpula et al. in "Engineering of Immunoglobulin Fc and Single Chain Fv Proteins in *Escherichia coli*" in *Antibody Expression and Engineering* (H. Y. Wang and T. Imanaka, eds.) American Chemical Society, pp 70–85 the contents of which are incorporated herein by reference. Both fragments were sequenced, and the 1.2 kb fragment was confirmed as encoding ADI by its partial homology to previously known genes encoding enzymes with ADI enzyme activity.

The five TGA codons in the isolated ADI gene which encode tryptophan in Mycoplasma were changed to TGG codons by oligonucleotide-directed mutagenesis according to the method of Sayers et al. *Biotechniques* 13: 592–596 (1992), the disclosure of which is incorporated herein by reference, prior to gene expression in *E. coli*. The GX6712/pGX9401 *E. coli* expression system used was the same as that described in the aforementioned Filpula et al. reference. Recombinant ADI was expressed in inclusion bodies at levels of 10% of the total cell protein.

B. Confirmation of N-Terminal Sequence of ADI Gene

In order to confirm the N-terminal region of the *M. arthritidis* gene corresponding to PCR primer SEQ ID NO:3, an independent PCR amplification of the N-terminal region was conducted using the established DNA sequence data from the first PCR. The technique employed was that of "inverse PCR" as described by H. Ochman et al., 1990, (*PCR PROTOCOLS: A GUIDE TO METHODS AND APPLICATIONS*, Academic Press, Inc., Eds., M. A. Innis, D. H. Gelfand et al.).

The inverse PCR was conducted using with PCR primers 5'-CTAAAACGGTTTCTAGTTCACC-3' (SEQ ID NO:5) and 5'-AGCGTGGAATTAATGTTGTTG-3' (SEQ ID NO:6). Two micrograms of genomic *M. arthritidis* DNA was digested with restriction endonuclease Sau 3A, then fragments were circularized by treatment with T4 DNA ligase. This DNA preparation was then subjected to PCR amplification using SEQ ID NOs 5 and 6. The amplified DNA was cloned and analyzed by DNA sequencing. DNA sequence analysis confirmed the assignment of serine as the amino acid following the initiation methionine (which is predicted to be post-translationally removed). Three silent base changes were also noted: Base 6 is A rather than T; Base 15 is T rather than C; Base 18 is C rather than T. In addition, Base 39 is T rather than C in this cloned sequence. None of these changes alters the translated protein sequence.

The three base differences between the N-terminal coding region of the confirmed genomic sequence and the SEQ ID NO:3 primer employed to isolate the gene are believed to account for the rather faint bands, as discussed above, that were produced when the PCR product was analyzed by gel electrophoresis. The three base differences are believed to have resulted in a poor annealing between the primer and the N-terminal coding region, resulting in a weak PCR signal observed on gel electrophoresis. Thus, given this difference and the weak PCR signal, the successful amplification of the entire ADI gene by PCR required careful selection of PCR conditions and therefore successful isolation of the gene represented by SEQ ID NO:1 was unexpected.

Example 2
Renaturation and Purification of Recombinant ADI

In this example, the ADI protein obtained as result of Example 1 is renatured according to the techniques reported by Misawa et al., with minor modifications (Misawa et al., 1994 "High-Level Expression of Mycoplasma arginine deiminase in *Escherichia coli* and Its Efficient Renaturation As An Antitumor Enzyme" in J. Biotechnol. 36: 145–155, the contents of which are incorporated herein by reference in its entirety).

To begin, 100 grams of cell paste is resuspended in 800 ml of 10 mM $K_2PO_4$, pH 7.0, 1 mM EDTA (buffer 1) and the cells are disrupted by two passes in a Microfluidizer (Microfluidics Corp. Newton Mass.). Triton X-100 is added to achieve a final concentration of 4% (v/v). The homogenate is stirred for 30 minutes at 4 degrees C. and is then centrifuged for 30 minutes at 13,000 g. The pellet is collected and re-suspended in one liter of buffer 1 containing 0.5% Triton X-100. The solution is diafiltered against 5 volumes of denaturation buffer (50 mM Tris HCl, pH 8.5, 10 mM DTT) using hollow fiber cartridges with 100 kD retention rating (Microgon Inc. Laguna Hills, Calif.). Guanidine HCl is added to achieve a final concentration of 6M and the solution is stirred for 15 minutes at 4 degrees C. The solution is then diluted 100-fold into refolding buffer (10 mM K $O_4$, pH 7.0) and stirred for 48 hours at 15 degrees C. Particulates are removed by centrifugation at 13,000 g. The resultant supernatant is concentrated on a Q Sepharose Fast Flow (Pharmacia, Inc. Piscataway, N.J.) column pre-equilibrated in refolding buffer. ADI is eluted using refolding buffer containing 0.2M NaCl. The purification procedure yields ADI protein which is >95% pure as estimated SDS-PAGE analysis. About eight grams of pure renatured ADI protein are produced from 1 kilogram of cell paste, which corresponds to a yield of 200 milligrams of ADI per liter of fermentation.

Example 3
Arginine Deiminase Assay

ADI activity was determined by a minor modification of the method described by Oginsky et al. in "Isolation and Determination of Arginine and Citrulline" *Methods Enzymology* 3: 639–643 (1957), the disclosure of which is incorporated herein by reference. Ten microliter samples in 0.1M $Na_2PO_4$, pH 7.0 (BUN assay buffer) were placed in a 96 well microtiter plate, 40 microliters of 0.5M arginine in BUN assay buffer was added and the plate was covered and incubated at 37° C. for 15 minutes. 200 microliters of complete BUN reagent (Sigma Diagnostics) was added and the covered plate was incubated for 10 minutes at 100° C. The plate was cooled to 22° C. and analyzed at 490 nm by a microtiter plate reader (Molecular Devices, Inc.). One IU is the amount of enzyme which converts 1 micromole of L-arginine to L-citrulline per minute. Protein concentrations were determined using Pierce Coomassie Plus Protein Assay Reagent (Pierce Co., Rockford, Ill.) with bovine serum albumin as standard. The specific enzyme activity of the purified ADI preparations was determined to be about 3 to about 30 IU/mg.

Example 4

In this example, succinimidyl carbonate-activated monomethoxypolyethylene glycol, molecular weight 12,000, was used to modify the arginine deiminase obtained as a result of Example 2. The succinimidyl carbonate activated mPEG was prepared in accordance with the method of the aforementioned U.S. Pat. No. 5,122,614.

A solution of arginine deiminase (0.910 mg in a volume of 1 ml) was adjusted to pH 8.0 with 100 mM borate buffer. A 50-fold molar excess of the activated PEG was dissolved in Water For Injection and then added to the arginine deiminase. The reaction was incubated at 4° C. for about 1 hour with continuous gentle mixing. After 1 hour, the reaction was stopped with an excess of arginine. The PEG-ADI conjugates were diafiltered through a Centriprep 30 with 15 volumes of 0.1 molar sodium phosphate, pH 7.0, which was monitored at 220 nm for the presence of the polymer until<0.05. The reaction products were analyzed as described in Example 3, supra, and found to have about 40% retained ADI activity.

Example 5

The process of Example 4 is repeated except that molecular weight 12,000 mPEG activated with an N-acyl thiazolidine is used.

Example 6

The process of Example 4 is repeated except that succinimidyl carbonate-activated monomethoxy-polyethylene glycol, molecular weight 5,000, is used.

Example 7
$PEG_{12,000}$-ADI INHIBITION OF SK-MEL-2 CELL GROWTH

In this example, the PEG-ADI prepared in accordance with Example 4 was compared to PEG ADI conjugates made using ADI obtained from *M. arginini* in a cell growth inhibition assay. The *M. arginini* ADI was obtained in a similar fashion as that used to obtain the *M. arthritidis* ADI except that the *M. arginini* ADI was purified to a higher extent than the *M. arthritidis* ADI. In particular, the *M. arthritidis* ADI was extracted and refolded to about 60% purity but not processed through anion exchange chromatography. Processing through the anion exchange chromatography is expected to yield greater than 90% purity of the *M. arthritidis* ADI enzyme. The PEG-conjugation technique used to make the *M. arginini*-derived ADI conjugates was the same as that used in Example 4. In both cases, PEG MW 12,000 was used to make the conjugates.

Melanoma cells were growth in Minimum Essential Medium (Eagle) with 0.1 mM non-essential amino acids, 1 mM sodium pyruvate and Earle's salts; fetal bovine serum 10%. Following trypsinization, viable cells were counted by trypan blue exclusion. Cells ($10^4$) were added to each well in a total of 100 microliters in 96 well micro-titer plates. $PEG_{12,000}$-ADI conjugates were diluted by 2-fold serial dilution in complete media (0.1 ml) and added to each well. Plates were incubated at 37° C. in 5% $CO_2$ incubator. Cell growth at day 3 was measured by adding 1/10th volume of "alamar Blue" dye (Alamar Biosciences, Inc. Sacramento, Calif.). After five hours of incubation, the plates were read with a Molecular Device plate reader at 570–630 nm.

The *M. arginini* derived PEG-ADI conjugates were found to have an $IC_{50}$ of 0.00015 IU/ml while the *M. arthritidis*-derived PEG-ADI had an $IC_{50}$ of 0.00010 IU/ml. Thus, when normalized in units of IU/ml, the PEG-ADI derived from *M. arthritidis* is seen to have 150% of the potency of the PEG-ADI derived from *M. arginini*.

Example 8
SDS PAGE Analysis

An SDS-PAGE analysis was carried out to compare PEG$_{12,000}$-ADI conjugates prepared either with *M. arginini*-derived ADI or, in accordance with the present invention, with *M. arthritidis*-derived ADI. The results indicate that the *M. arthritidis* derived conjugates had a more uniform distribution of size and had a higher average molecular weight (and therefore had more PEG molecules attached per ADI subunit). While Applicants are not bound by theory, it is believed that the *M. arthritidis* derived ADI included a greater number of lysines upon which the PEG could covalently attach, and, perhaps more importantly, there are a sufficient number of lysines on this specific ADI which are not associated with the active site.

Example 9
Sequence Comparisons

In this example, the amino acid sequences and sequence alignment of various arginine deiminases were investigated. Turning to FIG. 3, it is noted that line "a" represents the *M. arthritidis* ATCC 14152 ADI used in accordance with the present invention. Line "b" represents *M. arginini* LBIF ADI. Line "c" represents *M. hominis* PG21 ADI and line "d" represents *M. orale* FERMBP-1970 ADI. The dashes indicate amino acids identical to those found in line "a". Dots indicate gaps. The percent of amino acid sequence identity to *M. arthritidis* ADI is:

*M. arginini*—87%

*M. hominis*—81%

M. orale—83%.

This level of non-homology between the encoded amino acid sequences of the respective genes indicates significant differences between the encoded proteins of the respective Mycoplasma species. The sites of lysine substitutions are dispersed and extensive, indicating great diversity in potential polymer conjugation sites.

While there have been described what are presently believed to be the preferred embodiments of the invention, those skilled in the art will realize that changes and modifications may be made thereto without departing from the spirit of the invention. It is intended to claim all such changes and modifications that fall within the true scope of the invention. Numerous references are cited in the specification, the disclosures of which are incorporated by reference in their entireties.

---

What is claimed is:

1. An isolated nucleic acid molecule encoding an arginine deiminase enzyme comprising an amino acid sequence of SEQ ID NO:2.

2. The isolated nucleic acid molecule of claim 1 comprising a nucleic acid sequence of SEQ ID NO:1.

3. An isolated nucleic acid molecule comprising a nucleic acid sequence according to SEQ ID NO:1 wherein said nucleic acid sequence is mutated by nucleotide substitutions selected from the group consisting of replacing C with T at nucleotide 39, replacing T with C at nucleotide 104, replacing G with A at nucleotide 206, replacing G with A at nucleotide 729, replacing A with G at nucleotide 337, replacing T with C at nucleotide 830, replacing T with C at nucleotide 1023, replacing T with A at nucleotide 6 replacing C with T at nucleotide 15 and replacing T with C at nucleotide 18, and combinations thereof.

4. The isolated nucleic acid molecule of claim 3 that encodes a protein comprising the amino acid sequence of SEQ ID NO:2.

5. The isolated nucleic acid molecule of claim 1 that is selected from the group consisting of an RNA molecule and a DNA molecule.

6. An isolated nucleic acid molecule that is complementary to the nucleic acid molecule of claim 1.

7. An expression vector comprising the nucleic acid molecule of claim 1 operably linked to a control sequence.

8. The expression vector of claim 7 wherein said control sequence comprises a promoter.

9. The expression vector of claim 8 wherein said promoter is inducible.

10. The expression vector of claim 7 wherein said promoter is selected from the group consisting of a beta-lactamase promoter, a lac promoter, a trp promoter, a phoA promoter, an araBAD promoter, a T7 promoter, derivatives of the lambda PL and PR promotor and an OL/PR hybrid promoter.

11. The expression vector of claim 7 selected from the group consisting of a plasmid, a phage and a cosmid.

12. A recombinant host cell comprising the nucleic acid molecule of claim 1.

13. The host cell of claim 12 that is prokaryotic.

14. The host cell of claim 12 selected from the group consisting of a prokaryotic host cell and a eukaryotic host cell.

15. The host cell of claim 12 selected from the group consisting of a bacterium and a yeast.

16. The host cell of claim 15, that is *Escherichia coli*.

17. A process for producing arginine deiminase comprising:

a) culturing the host cell of claim 12 and b) expressing arginine deiminase in said host cell.

18. A process for producing arginine deiminase comprising:

a) transforming or transfecting a host cell with the vector of claim 7;

b) culturing the transformed or transfected host cell; and c) expressing arginine deiminase in said cultured host cell.

19. The process of claim 18 further comprising recovering said expressed arginine deiminase.

20. The process of claim 19 wherein said arginine deiminase is recovered by a process comprising extracting said expressed arginine deiminase from said host cell and renaturing said expressed arginine deiminase.

21. The process of claim 18 wherein said expressed arginine deiminase protein has a pI of 5.25.

22. The process of claim 18 wherein said expressed arginine deiminase enzyme has serine as an N-terminal residue, wherein said N-terminal is determined following post-translational removal of methionine.

23. The process of claim 18 wherein said expressed arginine deiminase enzyme has two cysteines per subunit.

24. The process of claim 18 wherein said expressed arginine deiminase enzyme comprises the amino acid sequence of SEQ ID NO:2.

25. The process of claim 18 wherein said expressed arginine deiminase enzyme has a specific activity of from about 3 to about 30 IU/mg.

26. An isolated nucleic acid molecule that is amplified from the genome of *Mycoplasma arthritidis* ATCC 14152 by a polymerase chain reaction using a primer pair selected from the group consisting of SEQ ID NO:3, SEQ ID NO:4; and said isolated nucleic acid molecule encodes an inine deiminase enzyme.

27. The isolated nucleic acid molecule of claim 26 wherein said encoded arginine deiminase enzyme has a pI of 5.25.

28. The isolated nucleic acid molecule of claim 26 wherein said encoded arginine deiminase enzyme has serine as an N-terminal residue, wherein said N-terminal is determined following post-translational removal of methionine.

29. The isolated nucleic acid molecule of claim 26 wherein said encoded arginine deiminase enzyme has two cysteines per subunit.

30. The isolated nucleic acid molecule of claim 26 wherein said encoded arginine deiminase enzyme comprises the amino acid sequence of SEQ ID NO:2.

31. The isolated nucleic acid molecule of claim 26 wherein said encoded arginine deiminase enzyme has a specific activity of from about 3 to about 30 IU/mg.

32. The isolated nucleic acid molecule of claim 26 wherein SEQ ID NO:3 is modified at base 6 so that A is substituted for T; at base 15 so that T is substituted for C; and at base 18 so that C is substituted for T, and combinations thereof.

33. The isolated nucleic acid molecule of claim 26 that is selected from the group consisting of an RNA molecule and a DNA molecule.

34. The host cell of claim 26 that is a bacterium.

* * * * *

UNITED STATES PATENT AND TRADEMARK OFFICE
CERTIFICATE OF CORRECTION

PATENT NO. : 5,916,793
DATED : June 29, 1999
INVENTOR(S) : Filupa, et al.

It is certified that error appears in the above-identified patent and that said Letters Patent is hereby corrected as shown below:

On the title page, item 56, References Cited, Other Publications:
Weickmann, J., et al., "Arginine Deiminase from *Mycoplasma arthritidis*," *Journal of Biological Chemistry* 253(17): 6016-6026 (Sep. 1978): "6016-6026" should read --6010-6015--;

Smith, D., et al., "Arginine Deiminase from *Mycoplasma arthritidis*, " *Journal of Biological Chemistry* 253(17) 6010-6020 (Sep. 1978): "6010" should read --6016--;

Misawa, S., et al., "High-level expression of *Mycoplasma arginine* deiminase in *E. coli* and its Efficient Renaturation as an Anti-tumor Enzyme," *Journal of Biotechnology 36:145*-155 (1994): "demininase in E. coli an dits" should read --deiminase in E. coli and its--;

Sarkar, S., et al., "Arginine Auxotrophy in Melanomas Results from a Defect in Argininosuccinate Synthetase Expression," 1996 *Annual Retreat on Cancer Research in New Jersey, Abstract B-5* (May 1996): "Arginosuccinate" should read --Argininosuccinate--;

Kondo, et al., "Cloning and Sequence Analysis of the Arginine Deiminase gene from *Mycoplasma arginini*" *Mol Gen Genet.* 221:81-86 (1990): "Myucoplasma arginini" should read --Mycoplasma arginini--.

Column 3, line 32: "5-tryptophan" should read --5 tryptophan;

Column 7, line 51: "MRNA" should read --mRNA--;

UNITED STATES PATENT AND TRADEMARK OFFICE
CERTIFICATE OF CORRECTION

PATENT NO. : 5,916,793
DATED : June 29, 1999
INVENTOR(S) : Filupa, et al.

It is certified that error appears in the above-identified patent and that said Letters Patent is hereby corrected as shown below:

Column 15, line 33: "KO$_4$" should read --K$_2$PO$_4$--;

Column 34, line 57: "inine" should read --arginine--.

Signed and Sealed this

Ninth Day of May, 2000

Attest:

Q. TODD DICKINSON

Attesting Officer

Director of Patents and Trademarks

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 1230 base pairs
      (B) TYPE: nucleic acid
      (C) STRANDEDNESS: double
      (D) TOPOLOGY: Not Relevant (ii) MOLECULE TYPE: DNA (genomic)

(vi) ORIGINAL SOURCE:
      (A) ORGANISM: Mycoplasma arthritidis
      (B) INDIVIDUAL ISOLATE: EN231
      (C) CELL TYPE: unicellular organism (xi) SEQUENCE DESCRIPTION: SEQ ID NO:1:

```
ATG TCT GTA TTT GAC AGT AAA TTT AAG GGA ATT CAT GTC TAT TCA GAA        48
Met Ser Val Phe Asp Ser Lys Phe Lys Gly Ile His Val Tyr Ser Glu
 1               5                  10                  15

ATT GGT GAA CTA GAA ACC GTT TTA GTT CAC GAA CCT GGT AAA GAA ATT        96
Ile Gly Glu Leu Glu Thr Val Leu Val His Glu Pro Gly Lys Glu Ile
                20                  25                  30

GAT TAC ATT ACC CCA GCT CGT TTG GAT GAA TTA TTA TTC TCA GCT ATT       144
Asp Tyr Ile Thr Pro Ala Arg Leu Asp Glu Leu Leu Phe Ser Ala Ile
            35                  40                  45

CTA GAA AGC CAC GAT GCA AGA AAA GAA CAC AAA GAA TTC GTA GCA GAA       192
Leu Glu Ser His Asp Ala Arg Lys Glu His Lys Glu Phe Val Ala Glu
        50                  55                  60

CTT AAA AAG CGT GGA ATT AAT GTT GTT GAA TTA GTA GAT CTA ATC GTA       240
Leu Lys Lys Arg Gly Ile Asn Val Val Glu Leu Val Asp Leu Ile Val
 65                  70                  75                  80

GAA ACC TAT GAT TTA GCA TCA AAA GAA GCT AAA GAA AAA CTT TTA GAA       288
Glu Thr Tyr Asp Leu Ala Ser Lys Glu Ala Lys Glu Lys Leu Leu Glu
                85                  90                  95
```

```
GAA TTC CTA GAT GAT TCA GTA CCA GTT CTA TCA GAC GAA CAC CGT GCT      336
Glu Phe Leu Asp Asp Ser Val Pro Val Leu Ser Asp Glu His Arg Ala
            100                 105                 110

ACT GTT AAG AAA TTC TTA CAA AGT CAA AAA TCA ACA AGA TCA TTA GTT      384
Thr Val Lys Lys Phe Leu Gln Ser Gln Lys Ser Thr Arg Ser Leu Val
            115                 120                 125

GAA TAC ATG ATC GCA GGG ATC ACT AAA CAC GAT TTA AAA ATC GAA TCA      432
Glu Tyr Met Ile Ala Gly Ile Thr Lys His Asp Leu Lys Ile Glu Ser
            130                 135                 140

GAT TTA GAA TTA ATC GTT GAC CCA ATG CCT AAC TTG TAC TTC ACT CGT      480
Asp Leu Glu Leu Ile Val Asp Pro Met Pro Asn Leu Tyr Phe Thr Arg
145                 150                 155                 160

GAC CCA TTT GCA TCA GTA GGT AAT GGA GTT ACC ATC CAC TAC ATG CGT      528
Asp Pro Phe Ala Ser Val Gly Asn Gly Val Thr Ile His Tyr Met Arg
            165                 170                 175

TAC AAA GTA AGA CAA CGT GAA ACA TTA TTT AGC CGA TTT GTA TTT TCA      576
Tyr Lys Val Arg Gln Arg Glu Thr Leu Phe Ser Arg Phe Val Phe Ser
            180                 185                 190

AAT CAC CCT AAA CTA GTT AAT ACC CCA TGG TAC TAC GAC CCT GCT GAA      624
Asn His Pro Lys Leu Val Asn Thr Pro Trp Tyr Tyr Asp Pro Ala Glu
            195                 200                 205

GGA TTA ACA ATC GAA GGT GGA GAC GTA TTT ATC TAC AAT AAC GAT ACT      672
Gly Leu Thr Ile Glu Gly Gly Asp Val Phe Ile Tyr Asn Asn Asp Thr
            210                 215                 220

TTA GTA GTT GGT GTT TCA GAA AGA ACT GAC TTA CAA ACT ATT ACT TTA      720
Leu Val Val Gly Val Ser Glu Arg Thr Asp Leu Gln Thr Ile Thr Leu
225                 230                 235                 240

TTA GCT AAG AAC ATT AAA GCA AAT AAA GAA TGT GAA TTC AAA CGT ATT      768
Leu Ala Lys Asn Ile Lys Ala Asn Lys Glu Cys Glu Phe Lys Arg Ile
            245                 250                 255

GTA GCA ATT AAT GTT CCT AAA TGG ACA AAC CTA ATG CAC TTA GAC ACA      816
Val Ala Ile Asn Val Pro Lys Trp Thr Asn Leu Met His Leu Asp Thr
            260                 265                 270

TGG TTA ACA ATG CTA GAC AAA GAT AAA TTC TTA TAC TCA CCT ATT GCA      864
Trp Leu Thr Met Leu Asp Lys Asp Lys Phe Leu Tyr Ser Pro Ile Ala
            275                 280                 285

AAT GAT GTG TTT AAA TTC TGG GAC TAC GAT TTA GTT AAT GGC GGA GAC      912
Asn Asp Val Phe Lys Phe Trp Asp Tyr Asp Leu Val Asn Gly Gly Asp
            290                 295                 300

GCT CCT CAA CCA GTT GAC AAT GGA TTA CCT CTA GAA GAC TTA TTG AAA      960
Ala Pro Gln Pro Val Asp Asn Gly Leu Pro Leu Glu Asp Leu Leu Lys
305                 310                 315                 320

TCA ATC ATT GGT AAG AAA CCT ACT CTA ATT CCT ATT GCT GGT GCT GGT     1008
Ser Ile Ile Gly Lys Lys Pro Thr Leu Ile Pro Ile Ala Gly Ala Gly
            325                 330                 335

GCT TCA CAA ATC GAT ATT GAA CGT GAA ACC CAC TTT GAC GGA ACA AAC     1056
Ala Ser Gln Ile Asp Ile Glu Arg Glu Thr His Phe Asp Gly Thr Asn
            340                 345                 350

TAC CTA GCT GTA GCT CCT GGA ATT GTT ATT GGT TAT GCA CGT AAC GAA     1104
Tyr Leu Ala Val Ala Pro Gly Ile Val Ile Gly Tyr Ala Arg Asn Glu
            355                 360                 365

AAA ACA AAT GCC GCT TTA GAA GCT GCA GGA ATT ACT GTT CTA CCA TTC     1152
Lys Thr Asn Ala Ala Leu Glu Ala Ala Gly Ile Thr Val Leu Pro Phe
            370                 375                 380

AGA GGA AAC CAA CTT TCA CTT GGA ATG GGA AAT GCT CGT TGC ATG TCA     1200
Arg Gly Asn Gln Leu Ser Leu Gly Met Gly Asn Ala Arg Cys Met Ser
385                 390                 395                 400

ATG CCT CTA TCA CGT AAA GAT GTT AAG TGG                             1230
Met Pro Leu Ser Arg Lys Asp Val Lys Trp
            405                 410
```

(2) INFORMATION FOR SEQ ID NO:2:

(i) SEQUENCE CHARACTERISTICS:
        (A) LENGTH: 410 AMINO ACID RESIDUES
        (B) TYPE: AMINO ACID
        (D) TOPOLOGY: unknown (ii) MOLECULE TYPE: PROTEIN (vi) ORIGINAL SOURCE:
        (A) ORGANISM: Mycoplasma Arthritidis
        (B) INDIVIDUAL ISOLATE: EN231
        (C) CELL TYPE: unicellular organism (xi) SEQUENCE DESCRIPTION: SEQ ID NO:2:

```
Met Ser Val Phe Asp Ser Lys Phe Lys Gly Ile His Val Tyr Ser Glu
 1               5                  10                  15

Ile Gly Glu Leu Glu Thr Val Leu Val His Glu Pro Gly Lys Glu Ile
             20                  25                  30

Asp Tyr Ile Thr Pro Ala Arg Leu Asp Glu Leu Leu Phe Ser Ala Ile
             35                  40                  45

Leu Glu Ser His Asp Ala Arg Lys Glu His Lys Glu Phe Val Ala Glu
 50                  55                  60

Leu Lys Lys Arg Gly Ile Asn Val Val Glu Leu Val Asp Leu Ile Val
 65                  70                  75                  80

Glu Thr Tyr Asp Leu Ala Ser Lys Glu Ala Lys Glu Lys Leu Leu Glu
                 85                  90                  95

Glu Phe Leu Asp Asp Ser Val Pro Val Leu Ser Asp Glu His Arg Ala
                100                 105                 110

Thr Val Lys Lys Phe Leu Gln Ser Gln Lys Ser Thr Arg Ser Leu Val
             115                 120                 125

Glu Tyr Met Ile Ala Gly Ile Thr Lys His Asp Leu Lys Ile Glu Ser
130                 135                 140

Asp Leu Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
             180                 185                 190

Asn His Pro Lys Leu Val Asn Thr Pro Trp Tyr Tyr Asp Pro Ala Glu
             195                 200                 205

Gly Leu Thr Ile Glu Gly Gly Asp Val Phe Ile Tyr Asn Asn Asp Thr
210                 215                 220

Leu Val Val Gly Val Ser Glu Arg Thr Asp Leu Gln Thr Ile Thr Leu
225                 230                 235                 240

Leu Ala Lys Asn Ile Lys Ala Asn Lys Glu Cys Glu Phe Lys Arg Ile
                245                 250                 255

Val Ala Ile Asn Val Pro Lys Trp Thr Asn Leu Met His Leu Asp Thr
             260                 265                 270

Trp Leu Thr Met Leu Asp Lys Asp Lys Phe Leu Tyr Ser Pro Ile Ala
             275                 280                 285

Asn Asp Val Phe Lys Phe Trp Asp Tyr Asp Leu Val Asn Gly Gly Asp
290                 295                 300

Ala Pro Gln Pro Val Asp Asn Gly Leu Pro Leu Glu Asp Leu Leu Lys
305                 310                 315                 320

Ser Ile Ile Gly Lys Lys Pro Thr Leu Ile Pro Ile Ala Gly Ala Gly
                325                 330                 335
```

```
Ala Ser Gln Ile Asp Ile Glu Arg Glu Thr His Phe Asp Gly Thr Asn
            340                 345                 350

Tyr Leu Ala Val Ala Pro Gly Ile Val Ile Gly Tyr Ala Arg Asn Glu
            355                 360                 365

Lys Thr Asn Ala Ala Leu Glu Ala Ala Gly Ile Thr Val Leu Pro Phe
370                 375                 380

Arg Gly Asn Gln Leu Ser Leu Gly Met Gly Asn Ala Arg Cys Met Ser
385                 390                 395                 400

Met Pro Leu Ser Arg Lys Asp Val Lys Trp
            405                 410

(2) INFORMATION FOR SEQ ID NO:3:

(i) SEQUENCE CHARACTERISTICS:
        (A) LENGTH: 27 base pairs
        (B) TYPE: nucleic acid
        (C) STRANDEDNESS: both
        (D) TOPOLOGY: Not Relevant (ii) MOLECULE TYPE: other nucleic acid
        (A) DESCRIPTION: /desc = "oligonucleotide"

(iii) HYPOTHETICAL: NO (vi) ORIGINAL SOURCE:
        (A) ORGANISM: Mycoplasma arthritidis
        (B) STRAIN: ATCC 14152
        (C) INDIVIDUAL ISOLATE: EN231
        (G) CELL TYPE: unicellular (xi) SEQUENCE DESCRIPTION: SEQ ID NO:3:

GGCAATCGAT GTCTGTATTT GACAGTA                                          27

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: both
        (D) TOPOLOGY: Not Relevant (ii) MOLECULE TYPE: other nucleic acid
        (A) DESCRIPTION: /desc = "oligonucleotide"

(iii) HYPOTHETICAL: NO (vi) ORIGINAL SOURCE:
        (A) ORGANISM: Mycoplasma arthritidis
        (B) STRAIN: ATCC 14152
        (C) INDIVIDUAL ISOLATE: EN231
        (G) CELL TYPE: unicellular organism (xi) SEQUENCE DESCRIPTION: SEQ ID NO:4:

TGAGGATCCT TACTACCACT TAACATCTTT ACG                                   33

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: both
        (D) TOPOLOGY: Not Relevant (ii) MOLECULE TYPE: other nucleic acid
        (A) DESCRIPTION: /desc = "oligonucleotide"

(iii) HYPOTHETICAL: NO (iv) ANTI-SENSE: NO
```

(vi) ORIGINAL SOURCE:
  (A) ORGANISM: Mycoplasma arthritidis
  (B) STRAIN: ATCC 14152
  (C) INDIVIDUAL ISOLATE: EN231
  (G) CELL TYPE: unicellular organism (xi) SEQUENCE DESCRIPTION: SEQ ID NO:5:

CTAAAACGGT TTCTAGTTCA CC                                                22

(2) INFORMATION FOR SEQ ID NO:6:

(i) SEQUENCE CHARACTERISTICS:
    (A) LENGTH: 21 base pairs
    (B) TYPE: nucleic acid
    (C) STRANDEDNESS: both
    (D) TOPOLOGY: Not Relevant (ii) MOLECULE TYPE: other nucleic acid
    (A) DESCRIPTION: /desc = "oligonucleotide"

(iii) HYPOTHETICAL: NO (vi) ORIGINAL SOURCE:
    (A) ORGANISM: Mycoplasma arthritidis
    (B) STRAIN: ATCC 14152
    (C) INDIVIDUAL ISOLATE: EN231
    (G) CELL TYPE: unicellular organism (xi) SEQUENCE DESCRIPTION: SEQ ID NO:6:

AGCGTGGAAT TAATGTTGTT G                                                 21

(2) INFORMATION FOR SEQ ID NO:7:

(i) SEQUENCE CHARACTERISTICS:
    (A) LENGTH: 410 amino acids
    (B) TYPE: amino acid
    (C) STRANDEDNESS: Not Relevant
    (D) TOPOLOGY: unknown (ii) MOLECULE TYPE: protein (iii) HYPOTHETICAL: NO (vi) ORIGINAL SOURCE:
    (A) ORGANISM: Mycoplasma arginini
    (B) STRAIN: LBIF
    (G) CELL TYPE: unicellular organism (x) PUBLICATION INFORMATION:
    (A) AUTHORS: Ohno, et al.,
    (C) JOURNAL: Infection and Immunity
    (D) VOLUME: 58
    (F) PAGES: 3788-3795
    (G) DATE: November-1990

(xi) SEQUENCE DESCRIPTION: SEQ ID NO:7:

Met Ser Val Phe Asp Ser Lys Phe Lys Gly Ile His Val Tyr Ser Glu
 1               5                  10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Phe Ser Ala Ile
        35                  40                  45

Leu Glu Ser His Asp Ala Arg Lys Glu His Lys Ser Phe Val Ala Glu
 50                  55                  60

Leu Lys Ala Asn Asp Ile Asn Val Val Glu Leu Ile Asp Leu Val Ala
 65                  70                  75                  80

Glu Thr Tyr Asp Leu Ala Ser Gln Glu Ala Lys Asp Lys Leu Ile Glu
                85                  90                  95

```
Glu Phe Leu Asp Asp Ser Glu Pro Val Leu Ser Glu His Lys Val
            100                 105                 110
Val Val Arg Asn Phe Leu Lys Ala Lys Lys Thr Ser Arg Lys Leu Val
        115                 120                 125
Glu Ile Met Met Ala Gly Ile Thr Lys Tyr Asp Leu Gly Ile Glu Ala
    130                 135                 140
Asp His Glu Leu Ile Val Asp Pro Met Pro Asn Leu Tyr Phe Thr Arg
145                 150                 155                 160
Asp Pro Phe Ala Ser Val Gly Asn Gly Val Thr Ile His Tyr Met Arg
                165                 170                 175
Tyr Lys Val Arg Gln Arg Glu Thr Leu Phe Ser Arg Phe Val Phe Ser
            180                 185                 190
Asn His Pro Lys Leu Ile Asn Thr Pro Trp Tyr Tyr Asp Pro Ser Leu
        195                 200                 205
Lys Leu Ser Ile Glu Gly Gly Asp Val Phe Ile Tyr Asn Asn Asp Thr
    210                 215                 220
Leu Val Val Gly Val Ser Glu Arg Thr Asp Leu Gln Thr Val Thr Leu
225                 230                 235                 240
Leu Ala Lys Asn Ile Val Ala Asn Lys Glu Cys Glu Phe Lys Arg Ile
                245                 250                 255
Val Ala Ile Asn Val Pro Lys Trp Thr Asn Leu Met His Leu Asp Thr
            260                 265                 270
Trp Leu Thr Met Leu Asp Lys Asp Lys Phe Leu Tyr Ser Pro Ile Ala
        275                 280                 285
Asn Asp Val Phe Lys Phe Trp Asp Tyr Asp Leu Val Asn Gly Gly Ala
    290                 295                 300
Glu Pro Gln Pro Val Glu Asn Gly Leu Pro Leu Glu Gly Leu Leu Gln
305                 310                 315                 320
Ser Ile Ile Asn Lys Lys Pro Val Leu Ile Pro Ile Ala Gly Glu Gly
                325                 330                 335
Ala Ser Gln Met Glu Ile Glu Arg Glu Thr His Phe Asp Gly Thr Asn
            340                 345                 350
Tyr Leu Ala Ile Arg Pro Gly Val Val Ile Gly Tyr Ser Arg Asn Glu
        355                 360                 365
Lys Thr Asn Ala Ala Leu Glu Ala Ala Gly Ile Lys Val Leu Pro Phe
    370                 375                 380
His Gly Asn Gln Leu Ser Leu Gly Met Gly Asn Ala Arg Cys Met Ser
385                 390                 395                 400
Met Pro Leu Ser Arg Lys Asp Val Lys Trp
                405                 410

(2) INFORMATION FOR SEQ ID NO:8:

(i) SEQUENCE CHARACTERISTICS:
        (A) LENGTH: 410 amino acids
        (B) TYPE: amino acid
        (C) STRANDEDNESS: Not Relevant
        (D) TOPOLOGY: unknown (ii) MOLECULE TYPE: protein (iii) HYPOTHETICAL: NO (vi) ORIGINAL SOURCE:
        (A) ORGANISM: Mycoplasma hominis
        (B) STRAIN: PG21
        (G) CELL TYPE: unicellular (xi) SEQUENCE DESCRIPTION: SEQ ID NO:8:
```

```
Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Gln Glu Phe Val Lys Ile
    50                  55                  60

Met Lys Asp Arg Gly Ile Asn Val Val Glu Leu Thr Asp Leu Val Ala
65                  70                  75                  80

Glu Thr Tyr Asp Leu Ala Ser Lys Ala Lys Glu Glu Phe Ile Glu
                85                  90                  95

Thr Phe Leu Glu Glu Thr Val Pro Val Leu Thr Glu Ala Asn Lys Lys
                100                 105                 110

Ala Val Arg Ala Phe Leu Leu Ser Gln Lys Pro Thr His Glu Met Val
            115                 120                 125

Glu Phe Met Met Ser Gly Ile Thr Lys Tyr Glu Leu Gly Val Glu Ser
    130                 135                 140

Glu Asn Glu Leu Ile Val Asp Pro Met Pro Asn Leu Tyr Phe Thr Arg
145                 150                 155                 160

Asp Pro Phe Ala Ser Val Gly Asn Gly Val Thr Ile His Phe Met Arg
                165                 170                 175

Tyr Ile Val Arg Arg Arg Glu Thr Leu Phe Ala Arg Phe Val Phe Arg
            180                 185                 190

Asn His Pro Lys Leu Val Lys Thr Pro Trp Tyr Tyr Asp Pro Ala Met
        195                 200                 205

Lys Met Pro Ile Glu Gly Gly Asp Val Phe Ile Tyr Asn Asn Glu Thr
210                 215                 220

Leu Val Val Gly Val Ser Glu Arg Thr Asp Leu Asp Thr Ile Thr Leu
225                 230                 235                 240

Leu Ala Lys Asn Ile Lys Ala Asn Lys Glu Val Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asn Lys Phe Leu Tyr Ser Pro Ile Ala
    275                 280                 285

Asn Asp Val Phe Lys Phe Trp Asp Tyr Asp Leu Val Asn Gly Gly Ala
    290                 295                 300

Glu Pro Gln Pro Val Leu Asn Gly Leu Pro Leu Asp Lys Leu Leu Ala
305                 310                 315                 320

Ser Ile Ile Asn Lys Glu Pro Val Leu Ile Pro Ile Gly Gly Ala Gly
                325                 330                 335

Ala Thr Glu Met Glu Ile Ala Arg Glu Thr Asn Phe Asp Gly Thr Asn
            340                 345                 350

Tyr Leu Ala Ile Lys Pro Gly Leu Val Ile Gly Tyr Asp Arg Asn Glu
            355                 360                 365

Lys Thr Asn Ala Ala Leu Lys Ala Ala Gly Ile Thr Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

(2) INFORMATION FOR SEQ ID NO:9:
```

(i) SEQUENCE CHARACTERISTICS:
    (A) LENGTH: 410 amino acids
    (B) TYPE: amino acid
    (C) STRANDEDNESS: double
    (D) TOPOLOGY: Not Relevant (ii) MOLECULE TYPE:

(iii) HYPOTHETICAL: NO (iv) ANTI-SENSE: NO (vi) ORIGINAL SOURCE:
    (A) ORGANISM: Mycoplasma orale
    (B) STRAIN: FERM BP-1970
    (G) CELL TYPE: unicellular (xi) SEQUENCE DESCRIPTION: SEQ ID NO:9:

```
Met Ser Val Phe Ser Asp Lys Phe Asn Gly Ile His Val Tyr Ser Glu
1               5                   10                  15

Ile Gly Asp Leu Glu Ser Val Leu Val His Glu Pro Gly Leu Glu Ile
                20                  25                  30

Asp Tyr Ile Thr Pro Ala Arg Leu Asp Glu Leu Leu Phe Ser Ala Ile
            35                  40                  45

Leu Glu Ser Thr Asp Ala Arg Lys Glu His Lys Glu Phe Val Glu Glu
50                  55                  60

Leu Lys Lys Gln Gly Ile Asn Val Val Glu Leu Val Asp Leu Val Val
65                  70                  75                  80

Glu Thr Tyr Asn Leu Val Asp Lys Lys Thr Gln Glu Lys Leu Leu Lys
                85                  90                  95

Asp Phe Leu Asp Asp Ser Glu Pro Val Leu Ser Pro Glu His Arg Lys
                100                 105                 110

Ala Val Glu Lys Leu Leu Lys Ser Leu Lys Ser Thr Lys Glu Leu Ile
            115                 120                 125

Gln Tyr Met Met Ala Gly Ile Thr Lys Tyr Asp Leu Gly Ile Lys Ala
130                 135                 140

Asp Lys Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Asn Arg Glu Thr Leu Phe Ser Lys Phe Ile Phe Thr
                180                 185                 190

Asn His Pro Lys Leu Val Lys Thr Pro Trp Tyr Tyr Asp Pro Ala Met
            195                 200                 205

Lys Leu Ser Ile Glu Gly Gly Asp Val Phe Ile Tyr Asn Asn Asp Thr
210                 215                 220

Leu Val Val Gly Val Ser Glu Arg Thr Asp Leu Glu Thr Ile Thr Leu
225                 230                 235                 240

Leu Ala Lys Asn Ile Lys Ala Asn Lys Glu Cys Glu Phe Lys Arg Ile
                245                 250                 255

Val Ala Ile Asn Val Pro Lys Trp Thr Asn Leu Met His Leu Asp Thr
                260                 265                 270

Trp Leu Thr Met Leu Asp Lys Asp Lys Phe Leu Tyr Ser Pro Ile Ala
            275                 280                 285

Asn Asp Val Phe Lys Phe Trp Asp Tyr Asp Leu Val Asn Gly Gly Ser
290                 295                 300

Asn Pro Glu Pro Val Val Asn Gly Leu Pro Leu Asp Lys Leu Leu Glu
305                 310                 315                 320
```

-continued

```
Ser Ile Ile Asn Lys Lys Pro Val Leu Ile Pro Ile Ala Gly Lys Gly
                325                 330                 335

Ala Thr Glu Ile Glu Thr Ala Val Glu Thr His Phe Asp Gly Thr Asn
                340                 345                 350

Tyr Leu Ala Ile Lys Pro Gly Val Val Gly Tyr Ser Arg Asn Val
                355                 360             365

Lys Thr Asn Ala Ala Leu Glu Ala Asn Gly Ile Lys Val Leu Pro Phe
    370                 375                 380

Lys Gly Asn Gln Leu Ser Leu Gly Met Gly Asn Ala Arg Cys Met Ser
385                 390                 395                 400

Met Pro Leu Ser Arg Lys Asp Val Lys Trp
                405                 410
```